(12) United States Patent
Fugazza et al.

(10) Patent No.: US 9,907,868 B2
(45) Date of Patent: *Mar. 6, 2018

(54) PROCESS FOR THE PREPARATION OF COMPLEXES OF $^{68}$GA

(71) Applicant: ADVANCED ACCELERATOR APPLICATIONS S.A., Saint Genis Pouilly (FR)

(72) Inventors: Lorenza Fugazza, San Fiorano (IT); Maria Azzurra Filannino, Bertinoro (IT); Maurizio Franco Mariani, Ivrea (IT)

(73) Assignee: Advanced Accelerator Applications International S.A., Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/163,484

(22) Filed: May 24, 2016

(65) Prior Publication Data

US 2016/0263259 A1  Sep. 15, 2016

Related U.S. Application Data

(63) Continuation of application No. 14/237,728, filed as application No. PCT/EP2012/065659 on Aug. 10, 2012, now Pat. No. 9,375,498.

(30) Foreign Application Priority Data

Aug. 12, 2011 (IT) ................. FI2011A0180

(51) Int. Cl.
*A61K 51/04* (2006.01)
*A61K 51/08* (2006.01)
*C07B 59/00* (2006.01)

(52) U.S. Cl.
CPC ........ *A61K 51/0482* (2013.01); *A61K 51/088* (2013.01); *C07B 59/00* (2013.01); *C07B 59/008* (2013.01)

(58) Field of Classification Search
CPC .................................................. A61K 51/0482
USPC .......................................................... 540/465
See application file for complete search history.

(56) References Cited

FOREIGN PATENT DOCUMENTS

| | | |
|---|---|---|
| CN | 1874792 A | 12/2006 |
| WO | 2005009393 A2 | 2/2005 |
| WO | 2010092114 A1 | 8/2010 |

OTHER PUBLICATIONS

Velikyan et al., Bioconjugate Chem. (2008), vol. 19, pp. 569-573.*
Cited by applicant in the specification, pp. 2. lines 3-4.*
Hackh's Chem. Dict., 1969, pp. 605.*
International Search Report dated Mar. 13, 2013 in International Application No. PCT/EP2012/065659.
Written Opinion dated Mar. 13, 2013 in International Application No. PCT/EP2012/065659.

* cited by examiner

*Primary Examiner* — Taofiq A Solola
(74) *Attorney, Agent, or Firm* — LeClairRyan, a Professional Corporation

(57) ABSTRACT

A process for the preparation of complexes containing $^{68}$Ga wherein a buffer formic acid/formate in the presence of compounds capable to sequester metal cations is used in the complexation reaction.

11 Claims, No Drawings

US 9,907,868 B2

PROCESS FOR THE PREPARATION OF COMPLEXES OF $^{68}$GA

FIELD OF THE INVENTION

The invention deals with processes for preparing complexes containing isotopes, in particular complexes useful as radiomarkers containing the isotope $^{68}$Ga.

STATE OF THE ART

Despite the encouraging results of recent clinical studies using $^{68}$Ga-labelled radiotracer for PET imaging in vivo, the short half-life of the isotope (68 minutes) that doesn't allow a long-range distribution together with the need of an equipped "production radiopharmacy" for the labeling process still prohibit their widespread use in nuclear medicine routine.

The labeling with Ga-68 is carried out by complexing the radioactive metal with a suitable chelator in a reaction medium into which are introduced the radioactive dose of $^{68}$Ga driving from the elution of the $^{68}$Ga generator, the amount of the molecule to be labeled (referred as chelator-functionalized molecule or precursor in our application) and a suitable buffer to assure the optimal pH for the complexation.

The so called $^{68}$Ga generator is a resin commercially available and containing Germanium from which the wanted $^{68}$Ga is naturally formed by Germanium decay; therefore the elution of the resin, under the appropriate pH conditions, and in the presence of a chelator-functionalized molecule allows the formation of the wanted complex containing $^{68}$Ga; depending on the selected chelator-functionalized molecule, heating at 75-90° C. can be necessary.

The main limits to the success of the labeling are provided by the fact that the suitable pH must be kept constant and by the competition of the metallic impurities with the Ga-68 during the complexation process.

In view of the above said, the research of a suitable buffer capable of assuring a standard pH is obviously a topic subject continuously investigated by those skilled in the 68Ga-labelling and still open.

Such a buffer should be nontoxic, able to buffer in the pH range of 3.5-5.0, should not compete with gallium ions and preferentially have a weak metal complexing capacity.

Among the different buffer reported, the ones mainly used up to now are HEPES (sulfonic acid derivative) or acetate buffers; however, they allow working only in a strictly defined range of pH (Publication of Velikyan et al., Bioconjugate Chem., 2008, 19, 569-573) and may no longer retain the required buffer capacity when the eluate acidity slightly varies.

For example, even a little increase in the eluate volume coming from the generator cause the pH to turn to values which damage the complexation resulting in high amount of free Ga-68. This produces a risk of non-compliance that makes the final purification mandatory. Moreover, about the HEPES buffer no toxicological data are available: the final purification has to be performed also in order to remove, or at least reduce, the HEPES before the administration of the radiopharmaceutical. Others buffers have been recently proposed (WO 2010/092114) as efficient solution for the Ga-68 complexation, for instance lactate, tartrate and carbonate buffers. These buffers comprise at least two Ga-68 coordination functions overcoming the prejudice that they could interfere with the labeling. Anyway their use has been successfully tested with reduced and purified fractions of the generator eluate, without exempting from the pre-labeling treatment of the Ga-68 solution A second important limit is the competition of metallic impurities, mainly trivalent and bivalent cations deriving both from the stationary phase and from the Ga-68 decay (Zn). These metals are bound as well as the Ga-68 by the chelator-functionalized molecule reducing the number of molecules actually available for the labeling. This can result in an incomplete complexation of the Ga-68 reducing the final radiochemical purity of the preparation. In the prior art, sometimes the Ga-68 not complexed by the chelator-functionalized molecule during the labeling, is completely sequestered with the post-labelling addition of an excess of a chelator with recognized affinity for the isotope, (e.g. the EDTA chelator) in order to avoid the presence of high portion of free metals and to promote their elimination in case of administration of the radiopharmaceutical preparation (WO 2010/141833—Example 2). A partial Ga-68 complexation might be differently faced starting from higher amounts of chelator-functionalized molecule. However, an increase of the amount of chelated precursor produces an undesirable reduction of the specific radioactivity (ratio between the radioactive product and the not labeled product) that can worsen the diagnostic results. In fact, due to competition with the labeled molecule for the same receptor, the presence of unlabeled molecule may have a negative effect on the concentration of radioactivity in the target tissue. Hence, a high SRA (Specific Radioactivity) might be critical for providing a sufficient contrast in PET images between the target tissue and its surrounding. In the state of art, the presence of competing metallic ions is usually reduced by pre-purification or fractionation of the eluate before the labeling (as described by the patent No WO 2010/092114), but these steps provide a disadvantageous loss of starting activity. Moreover, if pre-labelling steps as well as the final purification cannot be avoided, the Ga-68 labeling will be always based, in some extent, on the automation, by using a synthesis module, making the kit strategy unfeasible. Beside the technical expertise needed, this require unfavorable prolonged time for the labeling. Due to short half-life of the radionuclide ($t_{1/2}$=68 minutes) and the limited activity provided by the generator, any improvement aimed to obtain a very rapid, direct and high-yielding complexation is highly desirable.

From all the above said it is clear the need of a process allowing the preparation of $^{68}$Ga complexes overcoming the above said problems.

SUMMARY OF THE INVENTION

A process for the preparation of complexes containing $^{68}$Ga wherein a buffer formic acid/formate, possibly in the presence of compounds capable to sequester metal cations, is used in the complexion reaction, is described.

DETAILED DESCRIPTION OF THE INVENTION

The present invention allows to overcome the above said problem through a process wherein the Ga-68 is effectively complexed by a chelator-functionalized molecule in an aqueous buffer formic acid/formate.

The above said buffer formic acid/formate not only allows to establish the right pH but also to tolerate the eluate volume/acidity variation.

In fact, its buffering capacity is centered at a pH value suitable for the Ga-68 complexation and it has no metal complexing capacity, so it doesn't provide interference with the labeling. Moreover, this buffer should be compatible with the pharmaceutical application because the formic acid is classified as class 3 (solvents with low toxic potential) residual solvent in the Pharmacopoeia for which a limit of 5 mg/ml (5000 ppm) is admitted.

Normally as formate sodium formate is preferred but also any other metallic salt of the formic acid can be used.

The ratio formic acid/formate is normally comprised between 1 and 3.5.

Moreover, in order to face the problem of the presence of metallic impurities, instead of increasing the amount of chelator-functionalized molecule (providing a reduction of the SRA) or pre-treating the generator eluate with time- and radioactivity-consuming purification steps, as it is the normal praxis in the art, it was found that sequestering agent can be used in the process in order to neutralize the interfering species leaving the Ga-68 more free to react with the chelator functionalized molecule.

These sequestering agents, if present, act as support chelator-functionalized molecule that temporarily or permanently subtract the competing metals to the reaction with the chelated-functionalized molecules.

It is worth noticing that the function of the sequestering agents in the present invention is opposite to the function of the sequestering agents used in the prior art, as described above.

In fact, according to the known procedures, at the end of the labeling a sequestering agent with particular affinity for the gallium can be added in order to chelate the not reacted portion of the isotope, while, according to the present invention, a sequestering agent able to minimize the competition of metallic impurities is added at the beginning of the reaction.

Obviously the sequestering agents used in the present invention should bind preferentially the competing metals rather than Ga-68 ion in order to avoid the interference with the main labeling reaction or the formation of by-side labeled species.

Moreover, according to a particular embodiment, the invention refers also to processes for complexing radioisotopes, and in particular $^{68}$Ga, wherein buffered solutions are used in combination with sequestering agents as above and hereinafter described.

According to the invention with chelator-functionalized molecules it is intended any molecule with targeting ability functionalized with a chelate able to complex radioactive isotopes such as Ga-68.

Preferred chelates for the complexation of Ga-68 according to the invention can be chosen among: DOTA and its derivatives, NOTA and its derivatives, PCTA and its derivatives.

Use may also be made, in general, of any chelate able to form a sufficiently stable cage around $Ga^{3+}$ in particular any aliphatic, macrocyclic or linear amine, or macrocycle amine with tertiary amines.

As molecule with targeting ability it is intended a molecule able to target a biological process of diagnostic or therapeutic interest, advantageously an amino acid, a peptide, advantageously comprising 4 to 15, or 4 to 10 amino acids, a polypeptide, a protein, a vitamin, a monosaccharide or polysaccharide, an antibody, a nucleic acid or an aptamer.

Among the molecules with targeting ability useful for the invention, we can mention (as example and not as limiting list):

Molecules targeting VEGF receptors
Bombesin analogs or molecules targeting GRP receptors
Molecules targeting somatostatin receptors
RGD peptides or αvβ3 and αvβ5 targeting molecules
Annexin V or molecules targeting apoptotic processes
Molecules targeting estrogen receptors
Molecules targeting atheroma plaque
The targeting molecules recalled in Topics in Current Chemistry, vol. 222, 260-274, Fundamentals of Receptor-based Diagnostic Metallopharmaceuticals, The sequestering agents, if present, are preferably chosen in the group consisting of:
glycine and other chelating aminoacids (for example methionine, cystein, etc . . . )
crown ethers and nitrogen crown ethers
eterocyclic organic compound e.g. 1,10-phenantroline, 2,2'-Bipyridine
calixarenes
polydentate chelator e.g. proteins, polysaccharides, and polynucleic acids
natural chelating agents e.g. catechins, tannin, porphyrin
in general linear or macrocyclic chelating agents (for example podands or kryptands)

Normally micromolar or, more advantageously nanomolar amounts of sequestering agent are used preferably less than 100 nanomolar, for example in a range of 20 and 25 nanomolar.

It is important to note that the sequestering agents as above explained can be advantageously utilized also in complexing reaction wherein other buffers are used.

Therefore it is another embodiment of the present invention a process comprising herein complexing reaction of radioactive isotopes, in particular $^{68}$Ga, wherein sequestering agents as above defined are added to the reaction buffer.

Preferably the complexing reaction is carried out in a pH range between 3 and 4.5, more preferably between 3.2 and 4.2, most preferably between 3.4 and 4.0.

The complexes obtained according to the process described above are also an embodiment of the present invention; they can contain formic acid/formate below 10 mg/ml and the sequestering agent (if used) below 100 nmols.

As said a commercial generator (consisting of a column of resin bearing Germanium) is eluted with an eluent containing an acid (normally HCL) directly into a vial containing buffer formate and a base.

A chelator-functionalized molecule (normally in the presence of a metals sequestering agent, as for example phenanthroline) is added into the vial and the reaction vial is heated for a short time; the product solution is collected and checked by reversed phase HPLC and ITLC (MeOH/ammonium acetate 1M 1/1).

The addition order can also be inverted.

For example the commercial generator can be eluted with an eluent containing an acid (normally HCl) directly in a vial containing a chelator-functionalised molecule (preferably in the presence of a metal sequestering agent, as for example a phenanthroline).

The formate buffer and the base are added in the vial and the reaction mixture is heated for a short time.

The acid eluate is normally constituted by an aqueous solution of a strong acid as for example HCl, while the base is an aqueous solution of a strong base as for example NaOH.

On the whole, the use of formate buffer guarantees a suitable pH even if variations in the eluate acidity occur and, in this way reduces, the amount of not complexed Ga-68 due to a too low or a too high pH resulting in high content of free $^{68}Ga^{3+}$ or $^{68}Ga$ hydroxides respectively. Moreover the addition of a sequestering agent allows to bring down the amount of chelator-functionalized molecule needed to obtain a complete Ga-68 complexation.

These two aspects enabled the applicant to achieve a suitable degree of complexation, advantageously at least 92%, 95% and 97%, and consequently a sufficient purity (at least 92%, 95% and 97%) without any kind of pre- or final purification. Since the results obtained confirm the feasibility of a direct Ga-68 labeling that doesn't require manipulation or purification, the formulation can be applied to the production of a specific kit.

Therefore, according to a particular embodiment the invention relates also to a kit comprising:

a siliconized vial containing the chelator-functionalized molecule and the selected sequestering agent;
a siliconized vial or a syringe containing a suitable ultra-pure formic acid/sodium formate mixture.

Moreover the invention relates also to a single vial containing the chelator-functionalized molecule, the selected sequestering agent and a suitable ultra-pure formic acid/sodium formate mixture.

EXAMPLE 1

$^{68}$GaDOTApeptide Labelling with 3 ml HCl 0.6M Eluate

A 30 mCi commercial generator (from IDB) having a $SnO_2$ stationary phase was eluted with 3 ml eluate of ultrapure HCl 0.6 M directly into a vial containing 200 ul of ultrapure buffer formate 1.5 M and ultrapure 400 ul of NaOH 4.5 M. Then 30 ug of DOTA-peptide and 4.5 ug of 1,10-phenantroline are added and the reaction vial is heated at 95° C. for 7 minutes. The product was checked by reversed phase HPLC and ITLC (MeOH/ammonium acetate 1M. 1/1) and the radiochemical purity resulted 98% in both tests.

EXAMPLE 2

$^{68}$GaDOTApeptide Labelling with 3.2 ml HCl 0.6M Eluate

A 30 mCi commercial generator (from IDB) having a $SnO_2$ stationary phase was eluted with 3.2 ml eluate of ultrapure HCl 0.6 M directly into a vial containing 200 ul of ultrapure buffer formate 1.5 M and ultrapure 400 ul of NaOH 4.5 M. Then 30 ug of DOTA-peptide and 4.5 ug of 1,10-phenantroline are added and the reaction vial is heated at 95° C. for 7 minutes. The product was checked by reversed phase HPLC and ITLC (MeOH/ammonium acetate 1M. 1/1) and the radiochemical purity resulted 97% in both tests.

EXAMPLE 3

$^{68}$GaDOTApeptide Labelling with 3 ml HCl 0.6 M Eluate

A 30 mCi commercial generator (from IDB) having a $SnO_2$ stationary phase was eluted with 3 ml eluate of ultrapure HCl 0.6 M directly into a vial containing 200 ul of ultrapure buffer formate 1.5 M and ultrapure 400 ul of NaOH 4.5 M. Then 30 ug of DOTA-peptide and 15 ug of 12-crown-4 are added and the reaction vial is heated at 95° C. for 7 minutes. The product was checked by reversed phase HPLC and ITLC (MeOH/ammonium acetate 1M. 1/1) and the radiochemical purity resulted respectively 98% and 96%.

EXAMPLE 4

$^{68}$GaDOTApeptide Labelling with 3 ml HCl 0.6 M eluate

A 30 mCi commercial generator (from IDB) having a $SnO_2$ stationary phase was eluted with 3 ml eluate of ultrapure HCl 0.6 M directly into a vial containing 30 ug of DOTA-peptide and 15 ug of 12-crown-4. Then 200 ul of ultrapure buffer formate 1.5 M and ultrapure 400 ul of NaOH 4.5 M are added and the reaction vial is heated at 95° C. for 7 minutes. The product was checked by reversed phase HPLC and ITLC (MeOH/ammonium acetate 1M. 1/1) and the radiochemical purity resulted respectively 98% and 96%.

The invention claimed is:

1. A process for the preparation of complexes of $^{68}$Ga, wherein the complexing reaction between a chelator-functionalized molecule selected from the group consisting of 1,4,7,10-tetraazacyclododecane-1,4,7,10-tretraacetic acid ("DOTA"); 1,4,7-triazacyclononane-1,4,7-triyltriacetic acid ("NOTA"); and 3,6,9,15-tetraazabicyclo[9.3.1]pentadeca-1(15),11,13-triene-3,6,9-triacetic acid ("PCTA") and $^{68}$Ga is carried out in a buffered aqueous solution, selected from the group consisting of acetate buffer, HEPES buffer, lactate buffer, tartrate buffer, and carbonate buffer in the presence of a compound capable of sequestering metal cations selected from the group consisting of glycine and other chelating amino acids, crown ethers and nitrogen crown ethers, heterocyclic organic compounds, calixarenes, polydentate chelators, natural chelating agents, catechins, tannins, porphyrinin, and linear or macrocyclic chelating agents, and wherein said compound able to sequester metal cations is added at the beginning of the complexing reaction.

2. The process according to claim 1, wherein the complexing reaction is carried out in a pH range between 3 and 4.5.

3. The process according to claim 2, wherein the reaction is carried out in a pH range between 3.2 and 4.2.

4. The process according to claim 2, wherein the reaction is carried out in a pH range between 3.4 and 4.0.

5. The process according to claim 1, wherein
a commercial generator of $^{68}$Ga is eluted with an eluate containing an acid directly into a vial containing the buffered aqueous solution;
a chelator-functionalized molecule is added into the vial;
the reaction vial is heated for a short time; and
complexes of $^{68}$Ga are collected.

6. The process according to claim 1, wherein
a commercial generator of $^{68}$Ga is eluted with an eluate containing an acid directly into a vial containing a chelator-functionalized molecule;
the buffered aqueous solution is added into the vial;
the reaction vial is heated for a short time; and
complexes of $^{68}$Ga are collected.

7. The process according to claim 6 wherein the acid eluate is an aqueous solution of HCl, and the base is an aqueous solution of NaOH.

8. Complexes of $^{68}$Ga obtained by the process according to claim 1, characterized in that they contain less than 10 mg/ml buffered aqueous solution and less than 100 nmols of the compound capable of sequestering metal cations.

9. A reaction kit comprising:
a first vial containing a chelator-functionalized molecule and a compound capable of sequestering metal cations; and
a second vial or a syringe containing a ultra-pure buffered aqueous solution.

10. The reaction kit according to claim 9, wherein said first and second vials are siliconized vials.

11. A vial containing a chelator-functionalized molecule, a compound capable of sequestering metal cations, and an ultra-pure buffered aqueous solution.

* * * * *